United States Patent [19]

Turner et al.

[11] Patent Number: 4,737,507

[45] Date of Patent: Apr. 12, 1988

[54] HETEROCYCLIC PENTALENE DERIVATIVES FOR USE IN COMBATING MICROORGANISMS

[75] Inventors: Susan J. Turner; Michael T. Clark, both of Sittingbourne, England

[73] Assignee: E. I. Du Pont de Nemours & Co., Wilmington, Del.

[21] Appl. No.: 883,663

[22] Filed: Jul. 9, 1986

[30] Foreign Application Priority Data

Jul. 19, 1985 [GB] United Kingdom ............... 8518213

[51] Int. Cl.$^4$ .................... A01N 43/02; C07D 291/08
[52] U.S. Cl. .................... 514/360; 548/100; 548/122; 548/123
[58] Field of Search ............ 548/122, 123, 100; 514/360

[56] References Cited

U.S. PATENT DOCUMENTS

| | | | |
|---|---|---|---|
| 4,440,564 | 4/1984 | Clark et al. ............ | 71/91 |
| 4,441,911 | 4/1984 | Clark et al. ............ | 71/90 |

Primary Examiner—Robert Gerstl

[57] ABSTRACT

The invention provides a method of combating a microorganism which comprises allowing a heterocyclic pentalene derivative of general formula I

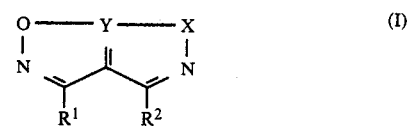

wherein X represents an oxygen atom, a sulphur atom or an —SO— moiety; Y represents a sulphur, selenium or tellurium atom, provided that when Y represents a selenium or tellurium atom X is an oxygen atom; and $R^1$ and $R^2$ together represent a —CH$_2$—C(CH$_3$)$_2$—CCl(CONH$_2$)— or —CH$_2$—A—CH$_2$— linkage where A is a —CH$_2$—, —CH(CH$_3$)— or —S(O)$_n$— moiety, where n is 0, 1 or 2; provided that when X is an oxygen atom and Y is a sulphur atom $R^1$ and $R^2$ together represent a —CH$_2$—S(O)$_n$—CH$_2$— linkage and when X is an —SO— moiety and A is a S(O)$_n$—, n is 2; to act on the microorganism or its environment; and such derivatives for use as a therapeutic substance.

6 Claims, No Drawings

HETEROCYCLIC PENTALENE DERIVATIVES FOR USE IN COMBATING MICROORGANISMS

This invention relates to heterocyclic pentalene derivatives for use in a method of combating microorganisms, and to such a method.

Certain oxadithiadiaza- and dioxathiadiaza-2,5-pentalenes having the following fused ring structure

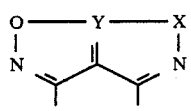

wherein Y is a sulphur and X is sulphur or oxygen are known from Perrier and Vialle, *Bull. Soc. Chim. France,* 1979, II-199–208 and Beer and Poole, *Tetrahedron Letters* No. 18, 1972, 1835–36. The references teach that the compound having this fused ring structure can be prepared by reacting a dioxime of a beta-diketone with sulphur monochloride or sulphur dichloride, the product typically being a mixture of the two ring systems. Certain dioxaselenadiaza- and dioxatelluradiaza-2,5-pentalenes wherein Y is selenium and tellurium and X is oxygen are also known from Perrier and Vialle, *Bull. Soc. Chim. France,* 1971 No. 12, 4591-2. None of the above references teach that the compounds described have any useful biological property.

EP-A-No. 68 557 discloses that certain oxadithiadiaza-, dioxaselenadiaza-, dioxatelluradiaza- and dioxathiadiaza-2,5-pentalenes have useful herbicidal properties. These heterocyclic pentalene derivatives are compounds of the general formula I or where possible an acid addition salt thereof:

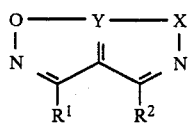

in which Y represents a sulphur, selenium or tellurium atom; $R^1$ and $R^2$ each independently represent an optionally substituted alkyl or aryl group or an alkoxycarbonyl group, or $R^1$ and $R^2$ together represent an alkylene linkage or an alkylene linkage containing a heteroatom in the chain, each linkage being optionally substituted with one or more alkyl groups or phenyl groups or an alkoxy substituted phenyl group, a benzyl group, an acyl group, a pyridyl group or a furyl group with the proviso that when the heteroatom is sulphur, it is optionally present in an oxidized form; and X represents an oxygen atom and in addition when Y represents a sulphur atom X optionally represents a sulphur atom.

None of the above references teaches or suggests that any of the heterocyclic pentalene derivatives might exhibit antimicrobial activity.

Microorganisms, e.g. bacteria, filamentous fungi, yeasts, microalgae and protozoa, may have deleterious effects in a variety of environments, e.g. industrial products and processes, public water supplies, swimming pools, humidifiers and cooling systems and catering and hospital environments. Sulphate-reducing bacteria can have deleterious effects in oil production and storage facilities. Pathogenic bacteria may cause diseases in human beings and animals. In combating microorganisms, an agent may be used which is biocidal or biostatic. In practice the distinction between biocidal and biostatic effect is usually one of concentration, the same agent being biocidal at higher concentrations and biostatic at lower ones.

It has now surprisingly been discovered that a specific sub-class of heterocyclic pentalene derivatives, which class includes some but not all of the class of compounds disclosed in EP-A-No. 68 557 as having herbicidal properties, has useful application in combating microorganisms. These compounds can be used both in combating pathogenic microorganisms in human beings and/or animals, or in combating microorganisms in industrial environments, e.g. the environments indicated above. They are active against a broad spectrum of microorganisms including gram-positive and gram-negative bacteria.

Accordingly, the present invention therefore provides a heterocyclic pentalene derivative of general formula I

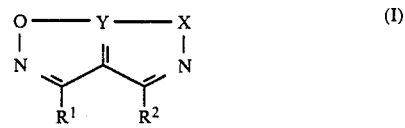

wherein X represents an oxygen atom, a sulphur atom or an —SO— moiety; Y represents a sulphur, selenium or tellurium atom, provided that when Y represents a selenium or tellurium atom X is an oxygen atom; and $R^1$ and $R^2$ together represent a —CH$_2$—C(CH$_3$)$_2$—CCl(CONH$_2$)— or —CH$_2$—A—CH$_2$ linkage where A is a —CH$_2$—, —CH(CH$_3$)— or —S(O)$_n$— moiety, where n is 0, 1 or 2; provided that when X is an oxygen atom and Y is a sulphur atom $R^1$ and $R^2$ together represent a —CH$_2$—S(O)$_n$—CH$_2$— linkage and when X is an —SO— moiety and A is —S(O)$_n$—, n is 2; for use as an active therapeutic substance. The substances are advantageously used in veterinary medicine.

Further, the invention provides a method of combating a microorganism which comprises allowing heterocyclic pentalene derivative as described above to act on the microorganism or its environment.

Preferred compounds of formula I for use in the invention have one or more of the following features:
(i) Y represents a sulphur atom and $R^1$ and $R^2$ together represent a —CH$_2$—S(O)$_n$—CH$_2$— linkage,
(ii) n is 2, and
(iii) X is a sulphur atom or an —SO— moiety.

A particularly useful application of the method of the invention lies in combating sulphate-reducing bacteria.

The invention also provides the use of a compound of formula I, as defined in the above method, in combating a microorganism.

In general, the compounds of formula I are either known compounds, as discussed above, or can be prepared by methods analogous to those for preparing the known compounds, e.g. those described in EP-A-No. 68557.

Certain compounds of formula I are novel. Accordingly the invention further provides compounds of formula I as defined above, wherein Y is a sulphur atom, and X is a sulphur atom and $R^1$ and $R^2$ together represent a —$CH_2$—$C(CH_3)_2$—$CCl(CONH_2)$— linkage or X is an —SO— moiety, preferably wherein $R^1$ and $R^2$ together represent a —$CH_2$—$SO_2$—$CH_2$— linkage.

The invention also provides a process for preparing a compound of formula I as defined above wherein X is an —SO— moiety which comprises treating a compound of formula I as defined in the above method with an oxidising agent, preferably a peracid, e.g. a perbenzoic acid such as meta-chloroperbenzoic acid. Reaction may conveniently be effected using a solvent such as chloroform, at ambient temperature.

Further in accordance with the invention there is provided a process for preparing a compound of formula I as defined in the above method wherein X and Y are both sulphur atoms and $R^1$ and $R^2$ together represent a —$CH_2$—$C(CH_3)_2$—$CCl(CONH_2)$— linkage which comprises reacting 4-cyano-5,5-dimethyl-1,3-cyclohexanedione dioxime with disulphur dichloride. Reaction may conveniently be effected at a temperature in the range from −65° C. to ambient temperature, e.g. in an ether solvent such as tetrahydrofuran.

When used for therapeutic purposes the compounds of formula I may be formulated for administration in any convenient way, by analogy with antibiotics and the invention therefore includes within its scope pharmaceutical compositions adapted for use in human or veterinary medicine. The compound is then present in a pharmaceutically pure form.

The pharmaceutical compositions may be presented in a form suitable for absorption by the gastro-intestinal tract, especially where the active ingredient exhibits oral absorption. Tablets and capsules for oral administration may be in unit dose presentation form, and may contain conventional excipients such as binding agents, for example, syrup, acacia, gelatin, sorbitol, tragacanth, or polyvinylpyrrolidone; fillers, for example, lactose, sugar, maize-starch, calcium phosphate, sorbitol or glycine; tabletting lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspensions, solutions, emulsions, syrups, or elixirs or may be presented as a dry product, for reconstitution with water or an other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example lecithin, sorbitan monooleate or acacia; non-aqueous vehicles which may include edible oils, for example, almond oil, fractionated coconut oil, oily esters, propylene glycol, or ethyl alcohol; preservatives, for example, methyl or propyl p-hydroxybenzoates or sorbic acid. Suppositories will contain conventional suppository bases, e.g. cocoa butter or other glycerides.

The compounds according to the invention may also be formulated for injection and may be presented in unit dose form, in ampoules, or in multi-dose containers, if necessary with an added preservative. The compositions may also take such forms as suspensions, solutions, or emulsions in oily or aqueous vehicles, and may contain formulatory agents such as suspending, stabilising and/or dispersing agents. Alternatively, the active ingredient may be in powder form for reconstitution with a suitable vehicle, e.g. sterile, pyrogen-free water, before use.

Compositions for veterinary medicine may, for example, for formulated as intramammary preparations in either long acting or quick release bases.

When employed in other, industrial environments, the compounds of formula I may, for example, be incorporated directly, or in the form of a concentrate composition, into products, e.g. liquid products such as water-based paints or adhesives, or aqueous environments such as cooling systems, storage tanks or oilfield production facilities, or they may be employed in liquid compositions for treatment e.g. of surfaces. In liquid environments the compounds of formula I may typically be employed in concentrations in the range 5 to 1000 mg/l (5 to 1000 ppm).

Anit-microbial compositions containing compounds of formula I may however be solid or liquid and contain inert solid or liquid carriers.

Suitable inert solid carriers may include talc, alumina, corn starch, diatomaceous earths and clays.

Suitable liquid carriers include water; alcohols e.g. methanol, isopropyl alcohol, isobutyl alcohol; glycols e.g. ethylene glycol; ketones e.g. acetone; ethyl oxalate; dimethylformamide; dimethylacetamide; liquid hydrocarbons e.g. kerosene; organic acids e.g. acetic acid. Mixture of different liquids are often suitable.

Antimicrobial compositions are often formulated and transported in a concentrated form which is subsequently diluted by the user before application. The presence of small amounts of carrier which is a surface active agent facilitates this process of dilution. Thus preferably at least one carrier in such a composition is a surface-active agent. For example the composition may contain at least two carriers, at least one of which is a surface-active agent.

A surface-active agent may be an emulsifying agent, a dispersing agent or a wetting agent; it may be nonionic or ionic. Examples of surface-active agents include the sodium salts of polyacrylic acids and lignin sulphonic acids; the condensation products of fatty acids or aliphatic amines or amides containing at least 12 carbon atoms in the molecule with ethylene oxide and/or propylene oxide; fatty acids esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metals, preferably sodium salts, of sulphuric or sulphonic acid esters containing at least 10 carbon atoms in the molecule, for example sodium lauryl sulphate, sodium secondary alkyl sulphates, sodium salts of sulphonate castor oil, and sodium alkylaryl sulphonates such as sodium dodecylbenzene sulphonate; and polymers of ethylene oxide and copolymers of ethylene oxide and propylene oxide.

The antimicrobial compositions may for example be formulated as solutions, emulsifiable concentrates, emulsions, suspension concentrates, powders which are dissolved in a suitable diluent prior to use or as solids which provide slow release of the formulated invention. In general, such compositions may contain from 5–95% active ingredient, preferably between 10–50%, with the remainder being adjuvants conventionally employed in such compositions, i.e. inert carriers, additives such as stabilizers (e.g. magnesium chloride, magnesium nitrate and cupric nitrate) and/or surface active agents.

Compositions containing compounds of formula I may also contain other ingredients, for example, other compounds possessing biocidal properties and compatible compounds such as oxygen scavengers, corrosion inhibitors and scale inhibitors.

The invention will be further understood from the following Examples, of which Examples 1 and 2 relate to synthesis of certain compounds of formula 1 and Example 3 demonstrates activity of compounds of formula I in combating microorganisms.

EXAMPLE 1

Preparation of 5H,7H-2-oxa-2a,3,6-trithia(2a-$S^{IV}$)-1,4-diazacyclopent[cd]indene-3-oxide 6,6-dioxide (Compound A)

The compound of Example 14 of EP-A-No. 68 557, 5H,7H-2-oxa-2a,3,6-trithia(2a-$S^{IV}$)-1,4-diazacyclopent[cd]indene (4.1 g, 20 mmol) was dissolved in chloroform (150 ml). To the resulting solution was added, with stirring, a solution of meta-chloroperbenzoic acid (11.9 g, 69 mmol) in chloroform (15 ml) and the mixture was stirred for 18 hours at ambient temperature (20° C.). A further quantity of meta-chloroperbenzoic acid (1.8 g, 11 mmol) in chloroform (25 ml) was added, and stirring continued at ambient temperature for a further 18 hours. The chloroform was evaporated off under reduced pressure, the residue was dissolved in ethyl acetate, and the resulting solution was washed with saturated aqueous sodium bicarbonate, dried (Na$_2$SO$_4$) and evaporated below 40° C. to yield a residue which was chromatographed on a silica column using ethyl acetate as eluant. The first band eluted was collected and upon recrystallisation the title product (formula I; Y=S, X=SO, R$^1$ and R$^2$ together=—CH$_2$—SO$_2$—CH$_2$—) was obtained as metallic-looking golden leaflets, (2.3 g, 46%) mp 198° C. (decomp.).

Analysis C$_5$H$_4$N$_2$O$_4$S$_3$: Theory: 23.8 C, 1.6 H, 11.1 N. Found: 23.7 C, 1.5 H, 11.6 N.

EXAMPLE 2

Preparation of 6-carboxamido-6-chloro-7,8-dihydro-7,7-dimethyl-6H-[1,2,3]dithiazolo[4,5,1-hi][2,1,3]benzoxathiazole-3-$S^{IV}$ (Compound B)

(a) Sodium metal (11.5 g, 0.5 mol) was dissolved in dry ethanol (225 ml) at ambient temperature (20° C.). Ethyl cyanoacetate (60 g, 0.53 mol) was added dropwise with stirring at ambient temperature. To the resulting solution was added dropwise, with stirring, mesityl oxide, and the mixture was heated under reflux for 4 hours. After cooling, the mixture was extracted with diethyl ether to remove any unreacted starting material and acidified with 2M aqueous hydrochloric acid. The brown oil which separated out was extracted into diethyl ether, dried (Na$_2$SO$_4$) evaporated and triturated with 40°–60° C. petroleum ether to give a pale yellow solid, which on recrystallisation from diethyl ether gave 4-cyano-5,5-dimethyl-1,3-cyclohexanedione as a white crystalline solid (48.6 g, 58.9%) m.p. 130°–132° C.

Analysis C$_9$H$_{11}$NO$_2$: Theory: 65.45 C, 6.7 H, 8.5 N. Found: 65.8 C, 7.0 H, 8.6 N.

(b) 4-Cyano-5,5-dimethyl-1,3-cyclohexanedione (1.65 g, 10 mmol), hydroxylamine hydrochloride (1.4 g, 20 mmol) and sodium acetate (1.65 g, 20 mmol) were dissolved together in water (50 ml) and heated under reflux for 30 minutes. The solution was cooled to 0° C. and the resulting precipitate was filtered off and air dried to give a yellow powder, which on recrystallisation from water gave 4-cyano-5,5-dimethyl-1,3-cyclohexanedione dioxime as pale yellow needles (1.5 g, 77%) m.p. 139°–140° C., with softening at 105° C.

Analysis C$_9$H$_{10}$N$_3$O$_2$S$_2$: Theory: 55.4 C, 6.7 H, 21.5 N. Found: 54.8 C, 7.0 H, 21.4 N.

(c) 4-Cyano-5,5-dimethyl-1,3-cyclohexanedione dioxime (13.7 g, 70.25 mmol) was dissolved in dry tetrahydrofuran (300 ml) at −65° C. Disulphur dichloride (20.3 g, 150 mmol) was added dropwise, with stirring, at −65° C. and the resulting yellow-brown mixture was stirred for 16 hours before being allowed to warm to ambient temperature (20° C.). The mixture was poured into water, extracted with chloroform/methanol (9:1v/v) and dried (Na$_2$SO$_4$). Upon chromatography on a silica column, eluting with chloroform/methanol (9:1v/v), the deep orange band eluted was evaporated to yield the title product (formula I; Y=S, X=S, R$^1$ and R$^2$ together=—CH$_2$—C(CH$_3$)$_2$—CCl(CONH$_2$)—) as a pale orange powder (3.0 g, 14.6%) mp 228° C. (decomp.)

Analysis C$_9$H$_{10}$N$_3$O$_2$S$_2$: Theory: 37.0 C, 3.4 H, 14.4 N, 12.2 Cl. Found: 36.9 C, 3.1 H, 14.2 N, 12.1 Cl.

EXAMPLE 3

Activity of compounds of formula I in combating microorganisms was demonstrated by tests against the following microorganisms.

Gram positive bacteria:
 *Staphylococcus aureus* (Sa) (NCIB 6571)
 *Bacillus subtilis* (Bs)
Gram negative bacteria:
 *Escherichia coli* (Ec) (NCIB 9517)

Desulfovibrio sp. (Dsp) mixed culture of sulphate reducing bacteria ex Brent, North Sea)
Desulfovibrio salexigens (Ds) (NCIB 8364)
Yeast:
 Saccharomyces cerevisiae (Sc) (ATCC 9763)
Filamentous fungi:
 Aspergillus niger (An) (CMI 17454)
 Cladosporium resinae (Cr)
 (NCIB=National Collection of Industrial Bacteria, Torry Research Station, P.O. Box 31, 135 Abbey Road, Aberdeen, Scotland AB9 8DG)
 (ATOC=American Type Culture Collection, 12301 Parklawn Dr., Rockville, Md. 20852, USA)
 (CMI=Commonwealth Mycological Institute, Ferry Lane, Kew, Surrey, England)

Inocula of the above microorganisms were prepared as follows.

In respect of the pathogenic bacteria S. aureus, B. subtilis and E. coli, the microorganisms were cultured in 50 ml aliquots of a tryptone soya broth in 250 ml conical flasks at 30° C. on a rotary shaker at 200 rpm for 24 hours. Tryptone soya broth was prepared by adding 17 g pancreatic digest of casein, 3 g papaic digest of soyabean meal, 5 g of sodium chloride, 2.5 g of dipotassium hydrogen phosphate and 2.5 g of dextrose to 1 liter of distilled water, mixing and sterilising by autoclaving at 121° C. for 15 minutes. 1 ml aliquots of the resulting cultures were mixed with 99 ml of fresh tryptone soya broth and used as inocula for tests.

The sulphate-reducing bacteria Desulfovibrio sp. and D. salexigens were cultured in a modified Postgate's Medium B for 24 hours at 30° C. and used directly as an inoculum. The modified Postgate's Medium B consisted of 0.5 g dipotassium hydrogen phosphate, 1 g ammonium chloride, 1 g sodium sulphate, 5 g sodium lactate, 1 g yeast extract, 0.1 ml thioglycolic acid, 0.1 ml ascorbic acid, 0.5 g ferrous sulphate heptahydrate, 750 ml aged seawater and 250 ml distilled water, pH adjusted to 7.8, divided into aliquots and sterilised by autoclaving at 121° C. for 15 minutes.

Inocula of S. cerevisiae were prepared as for S. aureus, B. subtilis and E. coli, but using yeast malt broth in place of the tryptone soya broth. The yeast malt broth was prepared by suspending 3 g yeast extract, 3 g malt extract, 5 g peptone and 10 g dextrose in 1 liter of distilled water, warming to achieve solution and sterilising by autoclaving at 121° C. for 15 minutes.

Inocula of the fungi Aspergillus niger and Cladosporium resinae were prepared containing $5 \times 10^5$ conidia/ml in a potato dextrose broth. The potato dextrose broth was prepared by suspending 4 g potato extract and 20 g dextrose in 1 liter of distilled water, warming to achieve solution, separating into aliquots and sterilising by autoclaving at 121° C. for 15 minutes.

Stock solutions of the various text compounds were prepared containing 10,000 ppm (1%w) compound in distilled water (in cases where the compound did not dissolve, up to 4%v/v acetone was included in the stock solution). Tests showed that such levels of acetone had no observable adverse effects on growth of the above listed microorganisms). Test procedures were as follows, depending on whether or not the test was against sulphate reducing bacteria (Desulfovibrio sp. or D. salexigens)

(i) Sulphate-Reducing Bacteria Test Dilution Series

Duplicate aliquots (9.9 ml) of dilution series from the stock solutions of each compound were prepared in the modified Postgate's Medium B described above. These contained 25 and 50 ppm compound. These were then inoculated with 0.1 ml of inoculum of one of the sulphate-reducing bacteria described above. After incubation at 30° C., the presence or absence of growth—as indicated by a blackening of the medium due to ferrous sulphide production—was recorded at 2, 5 and 10 days. Compounds active at 25 ppm were further tested at the lower concentrations of 5, 10 and 15 ppm.

(ii) Dilution Series For Other Test Bacteria, Yeast and Filamentous Fungi

Duplicate dilution series from the stock solution of each compound were prepared in sterile distilled water. These contained 50, 100, 500, 1000 and 5000 ppm compound. To a series of 5 compartments of square petri dishes 0.3 ml of each test compound concentration was added together with 2.7 ml of one of the microbial inocula described above. This gave final concentrations of the test compound of 10, 50, 100 and 500 ppm. After incubation, in the dark, at 30° C. the dishes were examined for the presence or absence of growth. Bacterial and yeast culters were examined after 24 hours and 72 hours incubation and the fungal cultures after 3, 7 and 10 days.

Bacterial and yeast cultures were assesed as:
+++=good growth (equal to controls)
++=growth
+=poor growth
−=no growth.

Fungal cultures were assessed as:
+++=good mycelial growth and spore formation
++=mycelial growth with reduced sporulation
+=mycelial growth poor with no sporulation
−=no growth.

At the end of each test those compartments showing no growth were checked for microbiostatic or microbiocidal activity of the compound by streaking the dish contents onto a suitable agar medium. After incubation at 30° C. for 24 hours the plates were examined for the presence or absence of growth. By means of the above tests minimum inhibitory concentrations i.e. the minimum concentration at which no growth occurs, were determined for the various test compounds. For comparison purposes, the above tests were also made using standard commercial compounds. The standard used in relation to the sulphate-reducing bacteria was "XC-102" (trademark) (ex Petrolite), which is a 25%w/w solution of glutaraldehyde in water, and that used in relation to the other microorganisms was the broad spectrum antimicrobial "KATHON 893" (trademark) (ex Rohm & Haas), which comprises 2-n-octyl-4-isothiazolin-3-one.

Results of the various tests are given in Table I following. In the Table, a compound designation such as EU 1 refers to the compound of Example 1 of EP-A-No. 68 557.

TABLE I

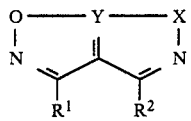

| Compound | X | R$^1$ R$^2$ | Y | Dsp | Ds | Sa | Bs | Ec | Sc | An | Cr |
|---|---|---|---|---|---|---|---|---|---|---|---|
| EU 1b, 2b | S | —CH$_2$—CH$_2$—CH$_2$— | S | 50 | <5 | 500 | 100 | 500 | <10 | <10 | <10 |
| EU 12 | S | —CH$_2$—CH(CH$_3$)—CH$_2$— | S | 25 | <5 | 500 | 100 | 500 | <10 | <10 | 25 |
| EU 13 | O | —CH$_2$—S—CH$_2$— | S | 50 | <5 | 500 | 500 | 500 | 500 | 25 | <10 |
| EU 14 | S | —CH$_2$—S—CH$_2$— | S | 15 | <5 | 500 | 25 | 500 | <10 | <10 | <10 |
| EU 24 | O | —CH$_2$—SO—CH$_2$— | S | 50 | <5 | 100 | 100 | 500 | 500 | 500 | 50 |
| EU 26 | S | —CH$_2$—SO$_2$—CH$_2$— | S | 10 | <5 | 500 | 50 | 500 | 500 | 500 | 50 |
| EU 33 | O | —CH$_2$—S—CH$_2$— | Se | 25 | | | | | | | |
| EU 35 | O | —CH$_2$—CH$_2$—CH$_2$— | Te | 15 | | <10 | <10 | <10 | <10 | <10 | <10 |
| Compound A | S=O | —CH$_2$—SO$_2$—CH— | S | 15 | <5 | 25 | 25 | 50 | 500 | >500 | 25 |
| Compound B | S | —CH$_2$—C(CH$_3$)$_2$—CCl(CONH$_2$)— | S | 25 | | 100 | 25 | 500 | >500 | >500 | >500 |
| COMPARATIVE | | | | | | | | | | | |
| Glutaraldehyde | | | | 25 | | | | | | | |
| 2-n-octyl-4-isothiazolin-3-one | | | | | | 500 | 100 | 500 | 50 | 100 | 100 |
| EU 1a, 2a | O | —CH$_2$—CH$_2$—CH$_2$— | S | * | | | | | | | |
| EU 3a, 4a | O | —CH$_2$—C(CH$_3$)$_2$—CH$_2$— | S | * | | | | | | | |
| EU 3b, 4b | S | —CH$_2$—C(CH$_3$)$_2$—CH$_2$— | S | * | | | | | | | |
| EU 5a, 6a | O | —CH(CH$_3$)—CH$_2$—CH(CH$_3$)— | S | * | | | | | | | |
| EU 5b, 6b | S | —CH(CH$_3$)—CH$_2$—CH(CH$_3$)— | S | * | | | | | | | |
| EU 7a | O | —CH$_2$—CH(C$_6$H$_5$)—CH$_2$— | S | * | | | | | | | |
| EU 7b | S | —CH$_2$—CH(C$_6$H$_5$)—CH$_2$— | S | * | | | | | | | |
| EU 9 | S | —CO$_2$C$_2$H$_5$—CH$_3$ | S | * | | | | | | | |
| EU 11 | O | —CH$_2$—CH(CH$_3$)—CH$_2$— | S | * | | | | | | | |
| EU 15 | O | —CH(C$_6$H$_5$)—CH(C$_6$H$_5$)—CH$_2$— | S | * | | | | | | | |
| EU 16 | S | —CH(C$_6$H$_5$)—CH(C$_6$H$_5$)—CH$_2$— | S | * | | | | | | | |
| EU 17 | O | —CH$_2$—CH(2-furyl)—CH$_2$— | S | * | | | | | | | |
| EU 18 | S | —CH$_2$—CH(2-furyl)—CH$_2$— | S | * | | | | | | | |
| EU 19 | O | —CH$_2$—CH(C$_6$H$_5$)—CH(C$_6$H$_5$)— | S | * | | | | | | | |
| EU 20 | S | —CH(C$_6$H$_5$)—C(CH$_3$)$_2$—CH$_2$— | S | * | | | | | | | |
| EU 21 | S | —CH$_2$—C(CH$_3$)$_2$—CH(C$_6$H$_5$)— | S | * | | | | | | | |
| EU 22 | O | —CH$_2$—CH(4-methoxyphenyl)-CH$_2$— | S | * | | | | | | | |
| EU 23 | S | —CH$_2$—CH(4-methoxyphenyl)-CH$_2$— | S | * | | | | | | | |
| EU 27 | O | —CH[CH(CH$_3$)$_2$]—S—CH$_2$— | S | * | | | | | | | |
| EU 28 | S | —CH[CH(CH$_3$)$_2$]—S—CH$_2$— | S | * | | | | | | | |
| EU 30 | S | —CH$_2$—N(benzyl)—CH$_2$— | S | * | | | | | | | |

*denotes no activity at 50 ppm; not tested against other microorganisms.

We claim:

1. A method of combating microorganisms which comprises presenting to the microorganism or its environment a heterocyclic pentalene derivative of general formula I

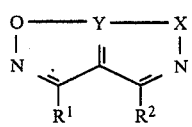

(I)

wherein X represents an oxygen atom, a sulphur atom or an —SO— moiety; Y represents a sulphur, selenium or tellurium atom, provided that when Y represents a selenium or tellurium atom X is an oxygen atom; and R$^1$ and R$^2$ together represent a —CH$_2$—C(CH$_3$)$_2$—CCl(CONH$_2$)— or —CH$_2$—A—CH$_2$ linkage where A is a —CH$_2$—, —CH(CH$_3$)— or —S(O)$_n$— moiety, where n is 0, 1 or 2; provided that when X is an oxygen atom and Y is a sulphur atom R$^1$ and R$^2$ together represent a —CH$_2$—S(O)$_n$—CH$_2$— linkage and when X is an —SO— moiety and A is —S(O)$_n$—, n is 2.

2. A method according to claim 1, wherein Y represents a sulphur atom and R$^1$ and R$^2$ together represent a —CH$_2$—S(O)$_n$—CH$_2$— linkage.

3. A method according to claim 2, wherein n is 2.

4. A method according to claims 1, 2 or 3, wherein X is a sulphur atom or an —SO— moiety.

5. A method according to claims 1, 2, 3 or 4, wherein the microorganism is a sulphate-reducing bacterium.

6. A heterocyclic pentalene derivative of general formula I

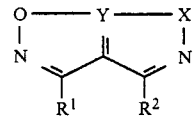

(I)

wherein Y is a sulphur atom, and X is a sulphur atom and R$^1$ and R$^2$ together represent a —CH$_2$C(CH$_3$)$_2$—CCl(CONH$_2$)— linkage or X is an —SO— moiety.

* * * * *